United States Patent
Jerichow

(10) Patent No.: US 11,712,965 B2
(45) Date of Patent: Aug. 1, 2023

(54) TRANSPORT DEVICE WITH AN OCCUPANT COMPARTMENT, COMPRISING AT LEAST ONE SENSOR FOR BREATH GAS ANALYSIS, AT LEAST ONE POSITION LOCATING DEVICE AND AT LEAST ONE DATA PROCESSING DEVICE

(71) Applicant: VitaScale GmbH, Nuremberg (DE)

(72) Inventor: Ulrich Jerichow, Gelnhausen (DE)

(73) Assignee: VitaScale GmbH, Nuremberg (DE)

( * ) Notice: Subject to any disclaimer, the term of this patent is extended or adjusted under 35 U.S.C. 154(b) by 206 days.

(21) Appl. No.: 17/027,143

(22) Filed: Sep. 21, 2020

(65) Prior Publication Data
US 2021/0113156 A1  Apr. 22, 2021

(30) Foreign Application Priority Data
Sep. 20, 2019 (DE) .......................... 102019125443.4

(51) Int. Cl.
*B60W 40/08* (2012.01)
*B60K 28/06* (2006.01)

(52) U.S. Cl.
CPC ............ *B60K 28/06* (2013.01); *B60K 28/063* (2013.01); *B60W 40/08* (2013.01); *B60W 2040/0818* (2013.01); *B60W 2040/0836* (2013.01); *B60W 2540/221* (2020.02); *B60W 2540/223* (2020.02); *B60W 2540/24* (2013.01)

(58) Field of Classification Search
CPC ..... B60K 28/06; B60K 28/063; B60W 40/08; B60W 2040/0818; B60W 2040/0836
See application file for complete search history.

(56) References Cited

U.S. PATENT DOCUMENTS

| | | | | |
|---|---|---|---|---|
| 6,479,019 B1 * | 11/2002 | Goldstein | .......... | G01N 33/4972 422/86 |
| 10,213,162 B2 * | 2/2019 | Fung | .................... | A61B 5/6893 |
| 2004/0154377 A1 * | 8/2004 | Stock | ..................... | A61B 5/097 73/23.3 |
| 2010/0025585 A1 * | 2/2010 | Taguchi | ............... | A61B 5/0059 73/23.3 |
| 2017/0263120 A1 * | 9/2017 | Durie, Jr. | ............... | G08G 1/205 |
| 2017/0274768 A1 * | 9/2017 | Hök | ................... | G01N 33/4972 |
| 2018/0074081 A1 * | 3/2018 | Wakana | ................. | H04N 23/51 |

FOREIGN PATENT DOCUMENTS

| | | |
|---|---|---|
| DE | 100 18 669 B4 | 11/2005 |
| DE | 10 2004 036 119 B4 | 6/2007 |
| DE | 10 2014 004 961 A1 | 10/2015 |
| DE | 10 2018 200 003 A1 | 7/2019 |

* cited by examiner

*Primary Examiner* — Benyam Haile
(74) *Attorney, Agent, or Firm* — Seed Intellectual Property Law Group LLP

(57) ABSTRACT

A transport device with an occupant compartment includes a control apparatus, a transport device door, a transport device roof, a safety belt, a transport device seat, a headset, a headrest, a rearview mirror, a sun visor, and/or a dashboard, as well as a sensor for breath gas analysis, a position locating device for determining the distance between the sensor and the front side of the head of a compartment occupant, a data processing device, and in some cases a sensor for measuring at least one vital sign. The sensor or sensors are present on or in the control apparatus, the transport device door, the transport device roof, the safety belt, the transport device seat, the headset, the headrest, the rearview mirror, the sun visor, and/or the dashboard, and the data processing device is in operative connection with a device for blocking the transport device and/or with an information output unit.

24 Claims, No Drawings

TRANSPORT DEVICE WITH AN OCCUPANT COMPARTMENT, COMPRISING AT LEAST ONE SENSOR FOR BREATH GAS ANALYSIS, AT LEAST ONE POSITION LOCATING DEVICE AND AT LEAST ONE DATA PROCESSING DEVICE

BACKGROUND

Technical Field

The present disclosure relates to a transport device with an occupant compartment, comprising at least one sensor for breath gas analysis, at least one position locating device for determining the distance between the sensor and the front side of the head of a compartment occupant, and at least one data processing device.

Description of the Related Art

Using and operating transport devices requires the utmost concentration. In the case of further traffic participants, such as, for example, in road or maritime traffic, it is imperative that the person at the control apparatus of a transport device has unimpaired judgment in order to be able to appropriately react to potential dangerous situations or changing traffic conditions. One cause of traffic accidents which is still not to be overlooked is the influence of alcohol and other drugs and the thereby impaired judgment of the traffic participants. But drowsiness, too, resulting, for example, from exceeding driving time limits, can lead to traffic accidents. Breathalyzers and vehicle operator monitoring systems for avoiding accidents are sufficiently known from the state of the art.

A number of systems include monitoring of vital signs of vehicle operators. DE 100 18 669 B4 discloses a driver state monitoring device for checking the physical state of a driver with a pulse sensor made of electrically conductive material arranged within a steering wheel. Through contact with the skin of the driver, this pulse sensor generates pulse signals which are compared with reference data of the driver in the normal state and communicated to the driver via a display device or audio signals. DE 10 2004 036 119 B4 describes a similar system with a driver assistance system for fatigue detection and attention evaluation of a driver. It is intended for the threat of incident microsleep to be detected through continuous recording of the pulse rate, wherein, upon a sudden change in pulse rate, a warning device is activated which emits acoustic and optical warning signals. Furthermore, an integrated storage device is intended to allow for statements to be made regarding the culpability of the driver in the case of a potentially occurring accident. Aside from their inaccuracy and error-prone nature, it is also a disadvantage of such systems that no statements can be made regarding potential alcohol consumption by the vehicle operator.

Alternative systems rely on determining the alcohol level of a vehicle operator right at the beginning of the drive, such as the system in DE 10 2014 004 961 A1. The device disclosed therein presents a hand-held device with a mouthpiece for taking a breath or saliva sample as well as an analysis unit for determining the alcohol concentration. In this case, the device is coupled to an immobilizer of the vehicle which prevents the starting or the operation of the vehicle. The disadvantage of such a hand-held device is that the breath gas monitoring can only be conducted once at the beginning of the drive, continuous monitoring with a handheld device is somewhat less feasible due to the hand thus removed from the control device and the view deviating from the road to the display of the hand-held device.

Further systems determine the air concentration inside the vehicle's interior. For example, DE 10 2018 200 003 A1 shows a method for analyzing the breath of vehicle occupants, wherein a time profile of a concentration of a breath gas inside the vehicle's interior is determined and evaluated. Furthermore, the method is intended to allow for measures to be taken to influence the vehicle occupants. The disadvantages of such systems are generally the measurements are averaged across the entire interior of the vehicle. No differentiation is made between breath air and ambient air.

Existing systems for checking and monitoring the driving ability of a driver always leave something to be desired. Thus, there is accordingly a need to be able to determine and check the state of vehicle occupants, such as regarding driving ability and driving fitness, reliably and throughout the entire duration of use of the vehicle, in some cases without negatively affecting the vehicle operator and/or the vehicle occupants.

DETAILED DESCRIPTION

Accordingly, the present disclosure provides a transport device with an occupant compartment, comprising a control apparatus, such as a steering wheel or steering column, at least one transport device door, a transport device roof, at least one safety belt, at least one transport device seat, at least one, in some cases wireless, headset, at least one headrest, at least one rearview mirror, at least one displaceable, in some cases foldable, sun visor, and/or a dashboard In some cases, the transport device includes a control apparatus, in some cases a steering wheel or steering column, at least one transport device door, a transport device roof and at least one transport device seat as well as optionally at least one safety belt, at least one rearview mirror, at least one displaceable, in some cases foldable, sun visor, at least one headrest, at least one, in some cases wireless, headset, and/or a dashboard, and further comprises:

a) at least one sensor, in some cases a plurality of sensors, for breath gas analysis,
b) at least one position locating device for determining the distance between the sensor and the front side of the head of a compartment occupant, in some cases of the compartment occupant at the control apparatus, and
c) at least one data processing device,
wherein the at least one sensor for breath gas analysis is present on or in the control apparatus, on or in the transport device door, on or in the transport device roof, on or in the safety belt, on or in the transport device seat, on or in the headset, on or in the headrest, on or in the rearview mirror, on or in the sun visor, and/or on or in the dashboard, and wherein the data processing device is in or is able to be brought into operative connection with a device for blocking the transport device and/or with an information output unit. In some embodiments, the transport device according to the present disclosure further includes, in addition to the at least one sensor for breath gas analysis, d) at least one sensor for measuring at least one vital sign. This sensor for measuring at least one vital sign can, in this case, also be present on or in the control apparatus, on or in the transport device door, on or in the transport device roof, on or in the safety belt, on or in the transport device seat, on or in the headset, on or in the headrest, on or in the rearview mirror, on or in the sun visor, and/or on or in the dashboard. In one embodiment, it is possible for the sensor for the breath gas analysis and for the sensor for measuring at least one vital sign to be present in the same place, for example on or in the control apparatus. It can also be provided that the sensor for the breath gas analysis and the sensor for measuring at least one vital sign are present in a combined sensor unit. In a further configuration, it can be provided that the sensor for the breath gas analysis is also adapted and arranged to determine at least one vital sign, in some cases in combination with the data processing device.

In an expedient configuration of the transport device according to the present disclosure, it is provided that the at least one sensor, in some cases the plurality of sensors, for breath gas analysis is adapted and arranged to qualitatively and quantitatively identify at least one substance selected from the group consisting of alcohols, such as ethanol, ketones, such as acetone, aldehydes, carboxylic acids, carbon oxides, nitrogen oxides, oxygen, hydrogen, water, and mixtures of these substances. Using the determination of the ethanol content, it can be established whether the vehicle operator can still be permitted to start the transport device. If, for example, the presence of hydrogen and/or ketones is detected, it is possible to draw conclusions about metabolism problems, which, if present, also contraindicate the starting and/or operation of the transport device. This, in operative connection with the data processing device, can lead to activation of the device for blocking the transport device and/or of an information output unit, depending on the predetermined setting of threshold values or threshold ranges.

Accordingly, it can be provided that the at least one sensor, in some cases the plurality of sensors, for breath gas analysis is or comprises an alcohol sensor, and/or that the at least one sensor, in some cases the plurality of sensors, for breath gas analysis is adapted and arranged to detect engine combustion gases.

In an expedient configuration the at least one sensor, in some cases the plurality of sensors, for breath gas analysis is adapted and arranged to determine the breathing rhythm, the depth of breath, and the breath frequency of the compartment occupants of the transport device, in some cases of the compartment occupant at the control apparatus. This allows, for example, for reliable determination of the degree of fatigue of a vehicle operator.

In a suitable embodiment of the transport device according to the present disclosure the at least one sensor, in some cases the plurality of sensors, for breath gas analysis is adapted and arranged to perform a breath gas analysis using a plurality of inhalations, in some cases using only one inhalation, in some further cases an inhalation at rest, of a compartment occupant of the transport device, in some cases of the compartment occupant at the control apparatus. With the transport device according to the present disclosure it is possible to perform the analysis of the breath gas with just one inhalation in order to draw conclusions regarding, for example, the driving fitness of a driver.

In at least one embodiment of the transport device according to the present disclosure, it can be provided that the at least one sensor, in some cases the plurality of sensors, for breath gas analysis is a component of a headset or sensor module. In this case, the transport device is one in which the headset or sensor module is removable, in some cases reversibly, from the control apparatus, the transport device door, the transport device roof, the safety belt, the transport device seat, the headrest, the rearview mirror, the sun visor, and/or the dashboard, wherein it is, in some cases, reversibly removable from the control apparatus, the transport device door, the transport device roof, the headrest, the rearview mirror, the sun visor, and/or the dashboard.

The at least one sensor for measuring at least one vital sign can be expediently adapted and arranged to determine the pulse, the heart rate, the skin conductance, the oxygenation of the blood, the sweat quantity, and/or the sweat composition of a compartment occupant, in some cases of the compartment occupant at the control apparatus.

With the transport device according to the present disclosure it is further possible in one embodiment to perform compartment occupant-specific measurements with the at least one sensor for breath gas analysis and/or the at least one sensor for measuring at least one vital sign.

In this case, it can be expediently provided that the at least one position locating device for determining the distance between the sensor and the front side of the head of a compartment occupant, in some cases the compartment occupant at the control apparatus, comprises at least one camera and/or infrared system.

In a further configuration, the transport device according to the present disclosure can further comprise at least one temperature sensor which is adapted and arranged to determine the temperature in the occupant compartment, and/or at least one humidity sensor which is adapted and arranged to determine the humidity in the occupant compartment, and/or at least one sensor which is adapted and arranged to determine the moisture in the exhaled breath of a compartment occupant, in some further cases of the compartment occupant at the control apparatus, and/or at least one flow sensor which is adapted and arranged to determine the airflow in the occupant compartment, in some cases if a ventilation or heating device is switched on.

In an expedient embodiment of the transport device according to the present disclosure, it is provided that the sensors, in some cases the sensor for breath gas analysis and/or the sensor for measuring the at least one vital sign, are adapted and arranged to determine measurement values, in some further cases the alcohol concentration, at the beginning of a transport and/or at defined temporal intervals during a transport, of a compartment occupant, in some cases of the compartment occupant at the control apparatus, and to transmit these values to the data processing device. In at least one configuration, the data processing device is adapted and arranged to compare the measurement values with stored reference values. In this case, the data processing device is adapted and arranged to activate the device for blocking the transport device and/or the information output unit upon determining a value which is higher than a stored threshold value.

In at least one configuration, the information output unit can be present in the transport device. Alternatively or additionally, the information output unit can also be present outside of the transport device and, for example, be wirelessly connected or connectible to the data processing device, for example with a hospital, an emergency medical station, a police station, and the like.

Furthermore, such transport devices according to the present disclosure have proven to be suitable which additionally have at least one camera unit, in some cases in operative connection with the data processing device, said camera unit being adapted and arranged for facial recognition of the driver of the transport device and/or of at least one occupant in the transport device and/or for recognizing the position of the mouth and/or nose relative to the at least one sensor.

The transport device according to the present disclosure can, for example, be selected from the group consisting of passenger motor vehicles, cargo motor vehicles, buses, trains/trams, ships, airplanes, forklifts, motorcycles, such as three-wheel motorcycles, and agricultural machines.

Using the transport device according to the present disclosure, it is surprisingly possible to reliably determine the state of driving fitness of an occupant of a transport device, such as of the vehicle operator, and, in response to the data determined and evaluated using a data processing device, to directly or indirectly make the occupant or occupants, such as the vehicle operator, aware of possible dangers and impairments to operating the transport device, or to prevent the starting or continuation of the actuation of the transport device. In this way, possible dangerous situations, for example too high a blood alcohol content or incurring fatigue, can very precisely be identified early and the risk of harm to humans and the environment can be significantly reduced.

The features of the present disclosure disclosed in the above description and in the claims can be substantial for the realization of the invention in its various embodiments both individually and in any combination.

The various embodiments described above can be combined to provide further embodiments. All of the patents and patent applications referred to in this specification and/or listed in the Application Data Sheet are incorporated herein by reference, in their entirety. Aspects of the embodiments can be modified, if necessary to employ concepts of the various patents and applications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled.

The invention claimed is:

1. A transport device with an occupant compartment, comprising:
    a control apparatus, at least one transport device door, a transport device roof, at least one safety belt, at least one transport device seat, at least one headset, at least one headrest, at least one rearview mirror, at least one displaceable sun visor, and/or a dashboard, the transport device further comprising:
    a) at least one sensor for breath gas analysis being adapted and arranged to determine a depth of breath of an occupant in the occupant compartment of the transport device and also being adapted and arranged to qualitatively and quantitatively identify ethanol and/or acetone,
    b) at least one position locating device for determining the distance between the at least one sensor and a front side of the head of the occupant in the occupant compartment,
    c) at least one temperature sensor which is adapted and arranged to determine a temperature in the occupant compartment, and
    d) at least one humidity sensor which is adapted and arranged to determine a humidity in the occupant compartment and/or moisture in the air exhaled by the occupant in the occupant compartment,
    e) at least one data processing device in communication with the at least one sensor, the at least one temperature sensor, and the at least one humidity sensor,
    wherein the at least one sensor for breath gas analysis is present on or in the control apparatus, on or in the transport device door, on or in the transport device roof, on or in the safety belt, on or in the transport device seat, on or in the headset, on or in the headrest, on or in the rearview mirror, on or in the sun visor, and/or on or in the dashboard, and
    wherein the data processing device is in or is able to be brought into operative connection with a device for blocking the transport device and/or with an information output unit,
    further comprising at least one flow sensor which is adapted and arranged to determine an airflow in the occupant compartment, if a ventilation or heating device is switched on.

2. The transport device according to claim 1, wherein the at least one sensor for breath gas analysis is adapted and arranged to qualitatively and quantitatively identify at least one substance selected from the group consisting of alcohols, ketones, aldehydes, carboxylic acids, carbon oxides, nitrogen oxides, oxygen, hydrogen, water, and mixtures of these substances.

3. The transport device according to claim 1, wherein the at least one sensor for breath gas analysis is or comprises an alcohol sensor and/or wherein the at least one sensor for breath gas analysis is adapted and arranged to detect engine combustion gases.

4. The transport device according to claim 1, wherein the at least one sensor for breath gas analysis is further adapted and arranged to determine a breathing rhythm and a breathing frequency of the occupant in the occupant compartment of the transport device.

5. The transport device according to claim 4, wherein the at least one sensor for breath gas analysis is adapted and arranged to determine the breathing rhythm and the breathing frequency of the occupant in the occupant compartment at the control apparatus.

6. The transport device according to claim 1, wherein the at least one sensor for breath gas analysis is adapted and arranged to perform a breath gas analysis using a plurality of breaths or only one breath of the occupant in the occupant compartment of the transport device.

7. The transport device according to claim 6, wherein the at least one sensor for breath gas analysis is adapted and arranged to perform a breath gas analysis using only one breath of the occupant of the occupant compartment of the transport device.

8. The transport device according to claim 1, wherein the at least one sensor for breath gas analysis is a component of a headset or sensor module.

9. The transport device according to claim 1, further comprising
    at least one sensor for measuring at least one vital sign which is adapted and arranged to determine a pulse, a heart rate, a skin conductance, an oxygenation of the blood, a sweat quantity, and/or a sweat composition of the occupant in the occupant compartment.

10. The transport device according to claim 9, wherein:
    the at least one sensor for measuring at least one vital sign is adapted and arranged to determine measurement values at the beginning of a transport and/or at defined temporal intervals during a transport, of the occupant in the occupant compartment, and to transmit these values to the data processing device, and
    the data processing device is adapted and arranged to compare the measurement values with stored reference values.

11. The transport device according to claim 1, wherein the at least one sensor for breath gas analysis and/or at least one sensor for measuring at least one vital sign is adapted and arranged to perform occupant-specific measurements of the occupant in the occupant compartment.

12. The transport device according to claim 1, wherein the at least one position locating device for determining the distance between the sensor and the front side of the head of the occupant in the occupant compartment comprises at least one camera and/or infrared system.

13. The transport device according to claim 1, wherein:
the at least one sensor is adapted and arranged to determine measurement values at the beginning of a transport and/or at defined temporal intervals during a transport, of the occupant in the occupant compartment, and to transmit these values to the data processing device and
the data processing device is adapted and arranged to compare the measurement values with stored reference values.

14. The transport device according to claim 1, wherein the data processing device is adapted and arranged to activate the device for blocking the transport device and/or the information output unit upon determining a value which is higher than a stored threshold value.

15. The transport device according to claim 14, wherein the information output unit is present in the transport device and/or outside of the transport device.

16. The transport device according to claim 1, further comprising
at least one camera unit which is adapted and arranged for facial recognition of a driver of the transport device and/or of at least one occupant in the transport device and/or for recognizing a position of the mouth and/or nose of an occupant of the occupant compartment relative to the at least one sensor.

17. The transport device according to claim 16, wherein the at least one camera unit is in operative connection with the data processing device.

18. The transport device according to claim 1, wherein the transport device is selected from a group consisting of passenger motor vehicles, cargo motor vehicles, buses, trains/trams, ships, forklifts, airplanes, motorcycles, and agricultural machines.

19. The transport device according to claim 1, wherein the control apparatus is a steering wheel or steering column.

20. The transport device according to claim 1, comprising:
a plurality of sensors for breath gas analysis.

21. The transport device according to claim 1, comprising:
at least one position locating device for determining the distance between the sensor and the front side of the head of the occupant in the occupant compartment at the control apparatus.

22. The transport device according to claim 1, wherein the at least one sensor for breath gas analysis is a component of a headset or sensor module which is reversibly removable from the control apparatus, the transport device door, the transport device roof, the safety belt, the transport device seat, the headrest, the rearview mirror, the sun visor, and/or the dashboard.

23. The transport device according to claim 1, wherein the at least one sensor is adapted and arranged to determine an alcohol concentration at the beginning of a transport and/or at defined temporal intervals during a transport of the occupant in the occupant compartment, and to transmit these values to the data processing device, wherein the data processing device is adapted and arranged to compare the measurement values with stored reference values.

24. The transport device according to claim 1, wherein the at least one sensor for breath gas analysis is adapted and arranged to determine the depth of breath of the occupant in the occupant compartment at the control apparatus.

* * * * *